(12) United States Patent
Damiano et al.

(10) Patent No.: US 7,806,854 B2
(45) Date of Patent: Oct. 5, 2010

(54) FULLY AUTOMATED CONTROL SYSTEM FOR TYPE 1 DIABETES

(75) Inventors: Edward Damiano, Acton, MA (US); Firas El-Khatib, Allston, MA (US)

(73) Assignees: Trustees of Boston University, Boston, MA (US); The Board of Trustees of the University of Illinois, Urbana, IL (US)

( * ) Notice: Subject to any disclaimer, the term of this patent is extended or adjusted under 35 U.S.C. 154(b) by 34 days.

(21) Appl. No.: 11/914,146

(22) PCT Filed: May 15, 2006

(86) PCT No.: PCT/US2006/018620

§ 371 (c)(1),
(2), (4) Date: Nov. 12, 2007

(87) PCT Pub. No.: WO2006/124716

PCT Pub. Date: Nov. 23, 2006

(65) Prior Publication Data

US 2008/0208113 A1 Aug. 28, 2008

Related U.S. Application Data

(60) Provisional application No. 60/681,128, filed on May 13, 2005, provisional application No. 60/735,568, filed on Nov. 10, 2005.

(51) Int. Cl.
*A61M 31/00* (2006.01)
(52) U.S. Cl. .......................................... 604/67
(58) Field of Classification Search ................ None
See application file for complete search history.

(56) References Cited

U.S. PATENT DOCUMENTS

| 4,280,494 | A | 7/1981 | Cosgrove et al. |
| 7,491,187 | B2 * | 2/2009 | Van Den Berghe et al. ... 604/66 |
| 2003/0181852 | A1 | 9/2003 | Mann et al. |
| 2003/0208113 | A1 | 11/2003 | Mault et al. |
| 2004/0028707 | A1 | 2/2004 | Pinkerton |

(Continued)

OTHER PUBLICATIONS

Albisser et al., "An Artificial Endocrine Pancreas," Diabetes 23 (1974): 389-396.

(Continued)

*Primary Examiner*—Nicholas D Lucchesi
*Assistant Examiner*—Pritesh Patel
(74) *Attorney, Agent, or Firm*—BainwoodHuang

(57) ABSTRACT

An augmented, adaptive algorithm utilizing model predictive control (MPC) is developed for closed-loop glucose control in type 1 diabetes. A linear empirical input-output subject model is used with an MPC algorithm to regulate blood glucose online, where the subject model is recursively adapted, and the control signal for delivery of insulin and a counter-regulatory agent such as glucagon is based solely on online glucose concentration measurements. The MPC signal is synthesized by optimizing an augmented objective function that minimizes local insulin accumulation in the subcutaneous depot and control signal aggressiveness, while simultaneously regulating glucose concentration to a preset reference set point. The mathematical formulation governing the subcutaneous accumulation of administered insulin is derived based on nominal temporal values pertaining to the pharmacokinetics (timecourse of activity) of insulin in human, in terms of its absorption rate, peak absorption time, and overall time of action.

45 Claims, 3 Drawing Sheets

U.S. PATENT DOCUMENTS

2004/0034295 A1    2/2004    Salganicoff
2004/0147872 A1    7/2004    Thompson

OTHER PUBLICATIONS

Bellazzi et al., "Adaptive Controllers for Intelligent Monitoring," Artif. Intell. Med. 7 (1995): 515-540.

Bellomo et al., "Optimal Feedback Glycaemia Regulation in Diabetics," Med. & Biol. Eng. & Comp. 20 (1982): 329-335.

Botz, "An Improved Control Algorithm for an Artificial β-Cell," IEEE Trans. Biomed. Eng. BME-23 (1976):252-255.

Brunetti et al., "A Simulation Study on a Self-Tuning Portable Controller of Blood Glucose," Int. J. Artif. Org. 16 (1993): 51-57.

Candas et al., "An Adaptive Plasma Glucose Controller Based on a Nonlinear Insulin/Glucose Model," IEEE Trans. Biomed. Eng. 41 (1994): 116-124.

Clemens, "Feedback Control Dynamics for Glucose Controlled Insulin Infusion Systems," Med. Prog. Technol. 6 (1979): 91-98.

Femat et al., "Blood Glucose Regulation: An Output Feedback Approach," Proc. IEEE Int. Conf. Control App. 1 (1999): 1290-1293.

Fischer et al., "Does Physiological Blood Glucose Control Require an Adaptive Control Strategy?" IEEE Trans. Biomed. Eng. BME-34 (1987): 575-582.

Fletcher et al., "Feasibility of an Implanted, Closed-Loop, Blood-Glucose Control Device," Immunology 230, Stanford University, Spring 01, 1-31.

Furler et al., "Blood Glucose Control by Intermittent Loop Closure in the Basal Mode: Computer Simulation Studies with a Diabetic Model," Diabetes Care 8 (1985): 553-561.

Kan et al., "Novel Control System for Blood Glucose Using a Model Predictive Method," ASAIO 4 (2000): 657-662.

Marliss et al., "Normalization of Glycemia in Diabetics During Meals with Insulin and Glucagon Delivery by the Artificial Pancreas," Diabetes 26 (1977): 663-672.

Pagurek et al., "Adaptive Control of the Human Glucose Regulatory System," Med. Biol. Eng. 10 (1972): 752-761.

Parker et al., "A Model-Based Algorithm for Blood Glucose Control in Type I Diabetic Patients," IEEE Trans. Biomed. Eng. 46 (1999): 148-157.

Parker et al., "The Intravenous Route to Blood Glucose Control," IEEE Eng. Med. & Biol. Jan./Feb. (2001): 65-73.

Parrish et al., "Control of an Artificial Human Pancreas Using the SDRE Method," Proc. American Control Conf. 2 (1997): 1059-1060.

Lauritzen et al., "Pharmacokinetics of Continuous Subcutaneous Insulin Infusion," Diabetologia, vol. 24, No. 5, May 1983, pp. 326-329.

Parker et al., "Model Predictive Control for Infusion Pump Insulin Delivery," Proceedings of the 18th Annual International Conference of the IEEE, vol. 6, 1996, pp. 1822-1823.

Trajanoski, "Neural Predictive Controller for Insulin Delivery Using the Subcutaneous Route," Biomedical Engineering, vol. 45, No. 9, 1998, pp. 1122-1134.

Supplementary European Search Report from EP06752536, search date Apr. 7, 2009.

* cited by examiner

FULLY AUTOMATED CONTROL SYSTEM FOR TYPE 1 DIABETES

BACKGROUND

Type 1 diabetes is a chronic, life-threatening disease that is caused by failure of the pancreas to deliver the hormone insulin, which is otherwise made and secreted by the beta cells of the pancreatic islets of Langerhans. Insulin opens receptors on the cell surfaces, thereby regulating inflow of blood glucose, an essential cell nutrient. With the resulting absence of endogenous insulin, people with type 1 diabetes cannot regulate their blood glucose to euglycemic range without exogenous insulin administration. However, it is critical to provide accurate insulin dosing, so as to minimize and whenever possible eliminate low or high blood glucose levels. Both high glucose levels, known as hyperglycemia, and low glucose levels, known as hypoglycemia, can have debilitating and deleterious consequences. Hypoglycemia may result in a coma and can cause acute complications, including brain damage and paralysis. While severe hyperglycemia can also result in a coma, mild chronic hyperglycemia potentially results in long-term, deleterious, and even life-threatening complications, such as vascular disease, renal complications, vision problems, nerve degeneration, and skin disorders.

In practice, it has been necessary for people with type 1 diabetes to monitor their blood glucose and administer exogenous insulin several times a day in a relentless effort to maintain their blood glucose near euglycemic range. This is a demanding, painstaking regimen. Even those who successfully adhere to the regimen are burdened by it to varying degrees and often still struggle with maintaining good glycemic control. Those who do not follow a regimen are at risk for severe complications.

SUMMARY

It would be desirable to reduce the burdens associated with monitoring blood glucose levels and administering exogenous insulin, as well as to better regulate blood glucose levels of those with type 1 diabetes and avoid the complications of hyper- and hypoglycemic conditions. A disclosed closed-loop control system automatically commands delivery of insulin based on glucose measurements. Since slight overdosing of insulin is possible during online operation of such a system, an agent having a counter-regulatory effect to insulin action, such as a hormone known as glucagon, is also made available for delivery by the system.

In a disclosed automated control system for type 1 diabetes, an adaptive algorithm utilizing model predictive control (MPC) is employed. An input-output subject model is used in conjunction with the MPC algorithm to regulate blood glucose online, where the subject model is recursively adapted, and the delivery of insulin is based solely on online glucose concentration measurements. An MPC signal is synthesized by optimizing an objective function that regulates glucose concentration to a preset reference set point while simultaneously minimizing both the control signal aggressiveness and local insulin accumulation in the subcutaneous space or "depot" that receives the infused insulin. A mathematical formulation describing the subcutaneous accumulation of administered insulin is derived based on nominal temporal values pertaining to the pharmacokinetics (time-course of activity) of insulin in human, in terms of its absorption rate, peak absorption time, and overall time of action. The MPC algorithm also provides control action with an integral effect, and in essence minimizes overall drug consumption. The control algorithm provides the automated glucose-control system with self-learning capability that enables it to operate under unrestricted activity of the subject.

The subject model may be an empirical subject model, which may initially be constructed based on a system identification process performed on input-output data obtained from open-loop glycemic control of the subject. The controller may be further operative to generate the insulin control signal to provide a basal rate of delivery of insulin when the model-predictive control algorithm reveals no need for a corrective dose of insulin.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
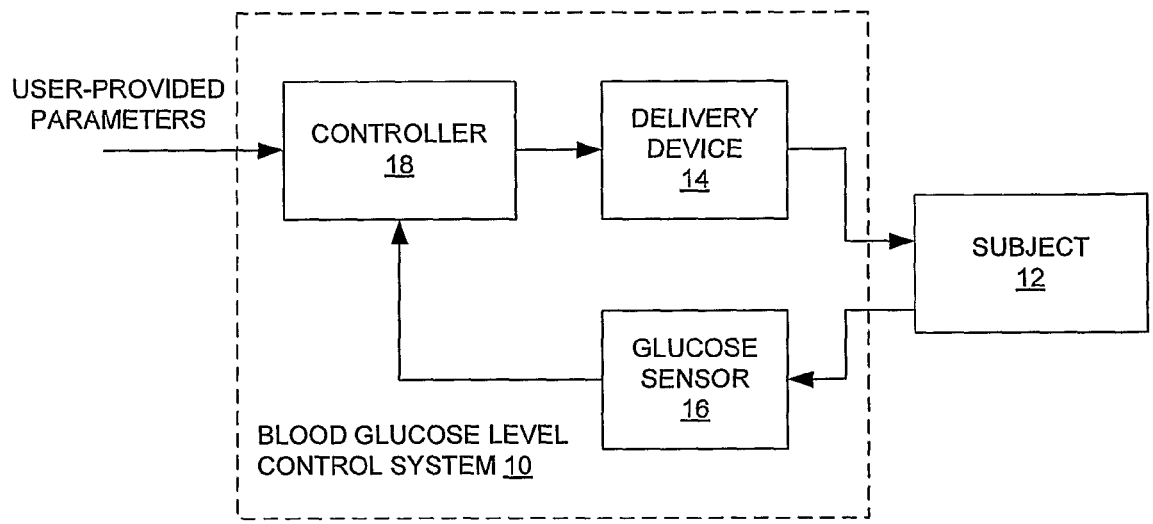
FIG. 1 is a block diagram of a fully automated control system for type 1 diabetes in accordance with the present invention.

FIG. 1 illustrates an automated control system 10 for regulating the blood glucose level of an animal subject (subject) 12, which may be a human. The subject 12 receives doses of insulin from a delivery device 14, which may be an infusion pump coupled by a catheter to a subcutaneous space of the subject 12 for example. As described below, the delivery device 14 may also deliver a counter-regulatory agent such as glucagon for more effective control of blood glucose level under certain circumstances. In the present description, reference is made to glucagon specifically, but it is to be understood that this is for convenience only and that other counter-regulatory agents may be used. For the delivery of both insulin and glucagon, the delivery device 14 is preferably a mechanically driven infusion mechanism having dual cartridges for insulin and glucagon respectively A glucose sensor 16 is operatively coupled to the subject 12 to continually sample a glucose level of the subject 12. Sensing may be accomplished in a variety of ways. A controller 18 controls operation of the delivery device 14 as a function of a glucose level signal from the glucose sensor 16 and subject to user-provided parameters. One feature of the disclosed technique is its ability to perform without receiving explicit information regarding either meals that the subject 12 has ingested or any other "feedforward" information. One necessary user-provided initialization parameter is the weight of the subject 12. Another user-provided parameter is a "setpoint" which, as described below, establishes a target blood glucose level that the system 10 strives to maintain.

Figure 2:
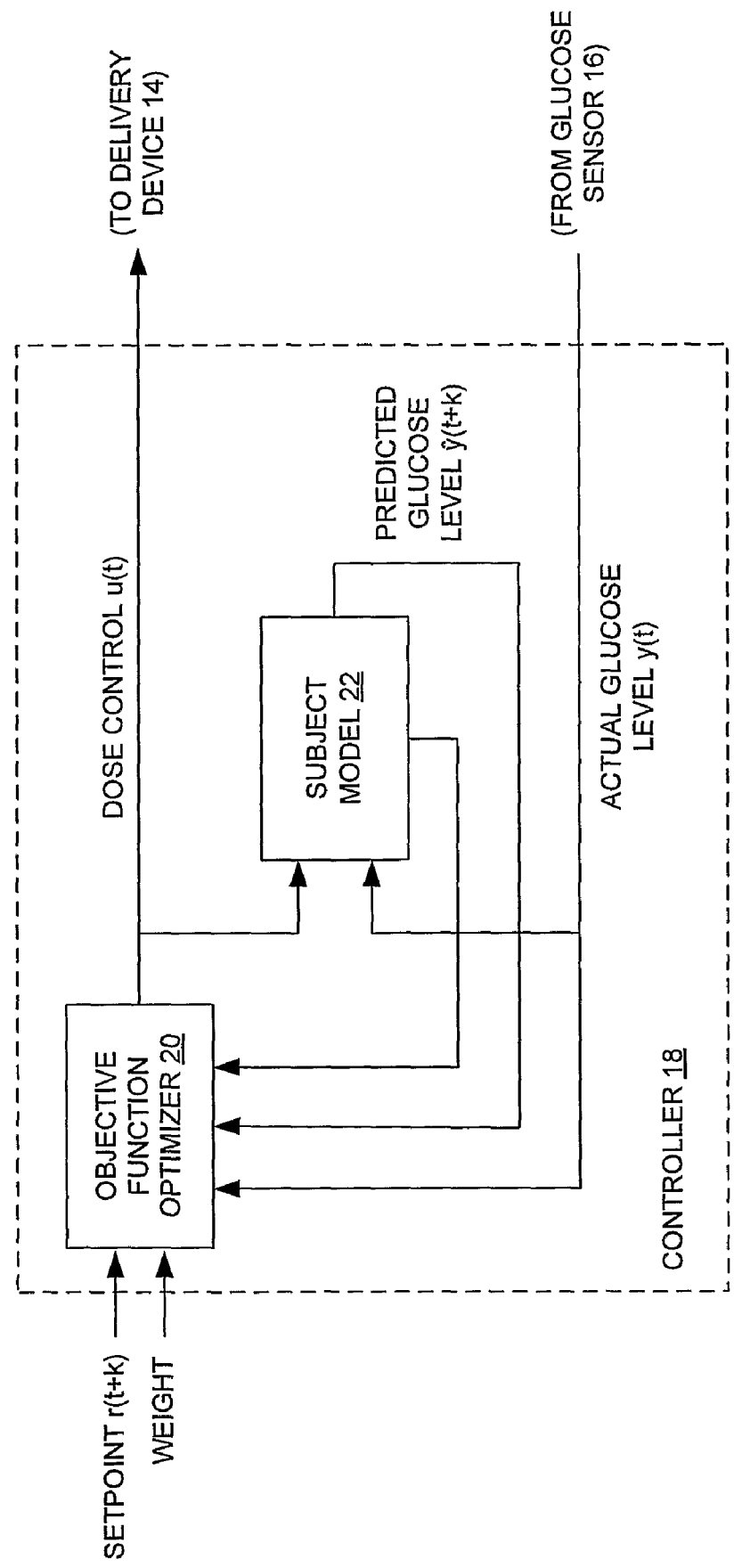
FIG. 2 is a functional block diagram of a controller in the system of FIG. 1.

FIG. 2 shows a functional block diagram of the controller 18, specifically a high-level depiction of a control algorithm that is executed by software/firmware within the controller 18. As shown, a dose control signal u(t) is generated by an objective function optimizer 20 which receives as one input a setpoint signal r(t+k), which may be constant (independent of time). The dose control signal u(t) controls the operation of the insulin-glucagon delivery device (delivery device) 14 of FIG. 1. The input dose control signal u(t) is also provided to a subject model 22 which, as described in more detail below, explicitly models the response of the subject 12 to delivery of insulin and/or glucagon. The subject model 22 also receives an actual glucose level signal y(t) from sensor 16, and generates a predicted future glucose level signal ŷ(t+k|t) that is used in the operation of the objective function optimizer 18.

During operation, the dose control signal u(t) and actual glucose level signal y(t) are continually fed into the subject model 22, thereby internally updating the subject model 22 and generating updated output predictions ŷ(t+k|t). By comparison with desired future reference setpoint values r(t+k), the objective function optimizer 20 computes future error signals which are used to synthesize the dose control signal u(t) in an optimizing fashion based on a model predictive control (MPC) algorithm. An amount of insulin or glucagon corresponding to the input signal u(t) is physically administered to the subject 12 via the delivery device 14 and is also passed to the subject model 22. The glucose sensor 16 provides the latest measurement y(t) to complete the cycle, which is then executed anew.

The function of the subject model 22 is to predict future blood glucose levels based on current and past values of the signals u(t) and y(t). There are a variety of models that can be employed. The following describes one particular embodiment for the subject model.

An option for the subject model is one of an empirical form, which may be obtained by system identification performed on input-output data generated from open-loop glycemic control of the subject. The subject model could be of a single-Input single-output, auto-regressive moving average with exogenous input (ARMAX) structure, with the representation $$A(z^{-1})y_t = z^{-d}B(z^{-1})u_t + C(z^{-1})w_t, \quad (1)$$

where $u_t$ denotes the (input) insulin-glucagon doses, $y_t$ denotes the (output) glucose concentration deviation from the reference set point, $w_t$ is a white Gaussian noise sequence, d is the inherent system time-delay (dead-time), $z^{-1}$ plays the role of the unit delay shift operator, and the scalar polynomials A, B, C are given by $$A(z^{-1}) = 1 + a_1 z^{-1} + a_2 z^{-2} + \ldots + a_n z^{-n},$$

$$B(z^{-1}) = b_0 + b_1 z^{-1} + b_2 z^{-2} + \ldots + b_m z^{-m},$$

$$C(z^{-1}) = 1 + c_1 z^{-1} + c_2 z^{-2} + \ldots + c_p z^{-p},$$

The model's orders and delay may be determined beforehand from the offline system identification analysis. The identified model is then employed in the online integrated control system, except that the model parameters are not statically stipulated, but are dynamic (free), in the sense that they are recursively updated. Recursive (online) parameter estimation of a model such as (1) may be facilitated by re-writing the model in regressor form, namely as $$y_t = \theta^T \psi_t + w_t, \quad (2)$$

where the the regressor $\psi_t$ and $\theta$ are respectively given by $$\psi_t := [-y_{t-1} \ldots -y_{t-n} u_{t-d} \ldots u_{t-d-m} w_{t-1} \ldots w_{t-p}]^T$$

$$\theta := [a_1 \ldots a_n b_0 \ldots b_m c_1 \ldots c_p]^T. \quad (3)$$

With online parameter estimates packed in a time-varying version of vector $\theta$, namely $\theta_t$, and the estimate $w_t := y_t - \psi_t^T \theta_t$ used in $\psi_t$, one popular recursive estimation scheme is the Extended Least Squares [13, 14], which follows the scheme $$\theta_t = \theta_{t-1} + \frac{P_{t-1} \psi_t}{1 + \psi_t^T P_{t-1} \psi_t} e_t \quad (4)$$

$$P_t = P_{t-1} - \frac{P_{t-1} \psi_t \psi_t^T P_{t-1}}{1 + \psi_t^T P_{t-1} \psi_t} \quad (5)$$

where $e_t := y_t - \psi_t^T \theta_{t-1}$, and $P_0$ is taken to be a positive definite matrix. Another option for recursive parameter estimation is the Recursive Maximum Likelihood estimation method, which is similar to the Extended Least Squares, except that $\phi_t := \psi_t/C(z^{-1})$ is used in lieu of $\psi_t$ [14]. Other recursive (online) parameter-estimation schemes may also be used, such as the Instrumental Variable method, the Gradient estimation method, or alternate versions of these estimators that use a forgetting factor, to mention but a few options known to those skilled in the art [14]. Regardless of the scheme used, the adaptive subject model can be used to make online predictions of glucose concentrations and can be inherently employed by the controller block in generating the control signal.

The function of the objective function optimizer 20 is to generate the insulin and glucagon control signals u(t) in an optimized fashion based in part on the predicted blood glucose levels ŷ(t+k|t) from the subject model 22. There are a variety of optimization techniques that can be used. The following describes one particular embodiment of the objective function optimizer 20, which is also referred to as the "controller block" in the following description. The embodiment described below uses a model-predictive control (MPC) strategy.

The controller block may use one or more of the many MPC strategies, which all (1) make use of a mathematical model to predict the output at future time instants (horizon), (2) compute the control signal that optimizes an objective function at each step, and (3) employ a receding horizon strategy [5, 8]. The latter aspect refers to repeatedly displacing the prediction horizon towards the future, while only applying the first control signal in the calculated sequence at each step.

One popular MPC algorithm, compatible with an ARMAX subject model, is the Generalized Predictive Control (GPC) algorithm, which optimizes the multi-stage quadratic cost function given by $$J_{GPC} = \sum_{k=N_d}^{N_m} \delta_k \|C(r_{t+k} - y_{t+k})\|^2 + \sum_{k=1}^{N_u} \lambda_k (\Delta u_{t+k})^2, \quad (6)$$

where $N_d$ and $N_m$ are respectively the minimum and maximum (output) prediction costing horizon limits, $N_u$ the control horizon bound, $\delta_m$ the weighting on prediction error, and $\lambda_n$ the weighting on control signals. Some general guidelines in GPC implementation include (1) $N_d \geq$ d, since earlier outputs are not influenced by the current input signal, (2) the output horizon, $N_y := N_m - N_d$, covering a substantial portion of the response rise time due to u(t|t), and (3) $N_y \geq N_u$, with $N_u = 0$ or square horizons, i.e $N_y = N_u$, popularly enforced.

For control action with integral effect, predictor and control design are based on $$A(z^{-1})y_t = z^{-k}B(z^{-1})u_t + C(z^{-1})w_t/\Delta, \quad (7)$$

with the corresponding Diophantine separation identity given by $$\frac{C}{A\Delta} = E_k + z^{-k}\frac{F_k}{A\Delta}, \quad (8)$$

where $F_k$ is the remainder polynomial corresponding to the monic quotient polynomial $E_k$, the former and latter of respective orders n and k−1 in $z^{-1}$, or specifically, $F_k = f_0 + f_1 z^{-1} + \ldots + f_n z^{-n}$ and $E_k = 1 + c_1 z^{-1} + \ldots + e_{k-1} z^{-(k-1)}$. The best predictor $\hat{y}_{t|t-k}$ is then defined to satisfy $$y_t = \hat{y}_{t|t-k} + E_k w_t, \quad (9)$$

which yields $$C\hat{y}_{t+k|t} = G_k \Delta u_{t+k-d} + F_k t_t, \quad (10)$$

where $G_k := E_k B$. Note that $G_k$ is order (m+k−1) in $z^{-1}$, and can be written as $G_k = g_0 + g_1 z^{-1} + \ldots + g_{m+k-1} z^{-(m+k-1)}$, with $g_0 = b_0$, since $E_k$ is monic $\forall k$. To implement the GPC algorithm, we re-write (10) as $$C\hat{y}_{t+k|t} = \sum_{i=0}^{k-d} g_i z^{-i} \Delta u_{t+k-d} + \left(G_k - \sum_{i=0}^{k-d} g_i z^{-i}\right) \Delta u_{t+k-d} + F_k y_t; \quad (11)$$

where the first term on the right-hand side contains the only k−d future-terms (containing the sought control signal) for any k. Taking $N_d = d$ and $N_y + 1 = N_u + 1 =: N$, i.e. square prediction and control horizons of N steps, we apply (11) over $k = d \rightarrow (N_y + d)$, and pack term contributions in the matrix-form equation given by $$y = Gu + G'u + Fy_t, \quad (12)$$

where $$y = \begin{bmatrix} C\hat{y}_{t+d|t} \\ C\hat{y}_{t+d+1|t} \\ \vdots \\ C\hat{y}_{t+N+d-1|t} \end{bmatrix}_{N\times 1} \quad G = $$

$$\begin{bmatrix} g_0 & 0 & 0 & \cdots & \cdot \\ g_1 & g_0 & 0 & \cdots & \cdot \\ \cdot & \cdot & \cdot & \cdots & \cdot \\ \cdot & \cdot & \cdot & \cdots & 0 \\ g_{N-1} & g_{N-2} & \cdots & \cdot & g_0 \end{bmatrix}_{N\times N} u = \begin{bmatrix} \Delta u_t \\ \Delta u_{t+1} \\ \cdot \\ \cdot \\ \Delta u_{t+1N-1} \end{bmatrix}_{N\times 1} G'u = $$

$$\begin{bmatrix} \left(G_d - \sum_{i=0}^{U} g_i z^{-i}\right) \Delta u_t \\ \left(G_{d+1} - \sum_{i=0}^{1} g_i z^{-i}\right) \Delta u_{t+1} \\ \vdots \\ \left(G_{N+d-1} - \sum_{i=0}^{N-1} g_i z^{-i}\right) \Delta u_{t+N-1} \end{bmatrix}_{N\times 1} F = \begin{bmatrix} F_d \\ F_{d+1} \\ \vdots \\ F_{N+d-1} \end{bmatrix}_{N\times 1}.$$

The last two quantities in (12) are available at time t, as they are either directly measurable or depend only on past measurements, and can be grouped into a vector f, leading to:

$$y = Gu + f, \quad (13)$$

With $\delta_m = 1$ and $\lambda_n = \lambda$, (6) can be re-written as $$J_{GPC} = (G + f - r)^T (G + f - r) + \lambda u^T u, \quad (14)$$

where r is the vector holding future set points as $r = [Cr_{t+d}\ Cr_{t+d+1}\ \ldots\ Cr_{t+N+d-1}]^T$. Further manipulation of (14) leads to $$J_{GPC} = \tfrac{1}{2} u^T H u + b^T u + f_0, \quad (15)$$

where $$H = 2(G^T G + \lambda I); \quad b^T = 2(f-r)^T G; \quad f_0 = (f-r)^T (f-r).$$

The unconstrained vector u minimizing $J_{GPC}$ can be found by inspection of (15), and is given by $$u_{GPC} = -H^{-1} b = (G^T G + \lambda I)^{-1} G^T (r - f). \quad (16)$$

Since $G^T G \geq 0$, (16) gives a unique solution, provided $\lambda > 0$. Only the first control move is of interest at t, namely $$\Delta u_t = [1\ 0\ 0\ \ldots\ 0](G^T G + \lambda I)^{-1} G^T (r - f). \quad (17)$$

The control increment or move in (17) is thus zero if the current situation and desired outcome coincide, that is if r−f=0, as it should. Finally, to deal with non-square horizons, which would only be permissible for $N_u < N_y$, G is replaced $G_{Nu}$, where $G_{Nu}$ is composed of the first $N_u + 1$ columns of G, and u is replaced by $u_{Nu}$, which contains the first $N_u + 1$ elements of u, with everything else kept the same. Note that the Generalized Minimum Variance (GMV) control, with $N_y = N_{u=N-}1 = 0$, is a special instance of GPC with square horizons.

In the case of subcutaneous drug administration, drug accumulation in the subcutaneous depot (typically that of insulin) can be augmented to the raw control cost function of (6), and viewed as an additional control objective in the optimization process. The resultant online control signal simultaneously (1) optimizes the controller's aggressiveness, (2) minimizes insulin accumulation in the subcutaneous depot, and (3) regulates glucose concentration to a preset set point target value. The mathematical formulation governing the subcutaneous accumulation of administered insulin can be derived based on nominal temporal values pertaining to its pharmacokinetics (time-course of activity), in terms of its absorption rate, peak absorption time, and overall time of action (perfusion into plasma). If p(t) is the concentration, in mU/dl, of the drug in plasma as it is absorbed from the subcutaneous depot, its evolution can be taken to be governed by $$p(t)=KU_0(e^{-\alpha_1 t}-e^{-\alpha_2 t}). \quad (18)$$

where $U_0$ is the subcutaneous-drug impulse dose in units (U), and K, $\alpha_1$, and $\alpha_2$ are positive constants. A measure of the pending effect of the accumulated amount of insulin in the SC depot can be taken to be the difference between the total area ($\int_0^\infty p(t)\,dt$, i.e. a measure of the total, action over time due to close $U_0$) and $\int_0^t p(t)\,dt$, i.e. a measure of the expended portion of $U_0$. With the measure of the lingering effect of the outstanding quantity of insulin in the SC depot denoted by q(t), we arrive at $$q(t) := \int_0^\infty p(t)\,dt - \int_0^t p(t)\,dt = \frac{KU_0}{\alpha_1 \alpha_2}(\alpha_2 e^{-\alpha_1 t} - \alpha_1 e^{-\alpha_2 t}); \quad (19)$$

As a discrete-time model, this can be written as $$\begin{aligned}q_k &= (e^{-\alpha_1 T_s} + e^{-\alpha_2 T_s})q_{k-1} - e^{-(\alpha_1+\alpha_2)T_s} q_{k-2} + \\ &\quad \frac{K}{\alpha_1 \alpha_2}(\alpha_2 - \alpha_1)u_{k-d_g} + \frac{K}{\alpha_1 \alpha_2} \\ &\quad (\alpha_1 e^{-\alpha_1 T_s} - \alpha_2 e^{-(\alpha_2 T_s)})u_{k-d_g-1} \\ &=: -\alpha_{1_q} q_{k-1} - \alpha_{2_q} q_{k-2} + b_{1_q} u_{k-d_q} + b_{2_q} u_{k-d_q-1},\end{aligned} \quad (20)$$

where $T_s$ is the sampling period. Incidently, IV dosing may be perceived as bypassing the SC depot, i.e. for an IV drug dose, q(t)=0 in (19) and $q_k$=0 in (20), as if there were zero peak ($\alpha_2 \to \infty$) and zero depletion or consumption times ($\alpha_1 \to \infty$) from the SC depot into plasma, with coinciding values for $\alpha_1$ and $\alpha_2$. Before augmenting (20) to the original discrete-time model of (1), whose inherent units are mg/dl, we non-dimensionalize (20) and re-scale it to switch its inherent units from mU min/dl to mg/dl, so that control signal computation (optimization) is performed on an overall homogenous (augmented) system. An overall scaling factor to operate on (20) can be obtained from the steady-state effect of an impulse dose on blood glucose, taken to vary as per a scaled integration of (18). As such, the scaling factor, $$s_f = \frac{y_\infty \alpha_1 \alpha_2}{U_0 K(\alpha_2 - \alpha_1)}\mathrm{1},$$

[1] Scaling factor $s_f$ provides the proper unit conversion, but can be scaled further by a unitless factor.

in mg/(mU min), where $y_\infty$ is the steady-state exclusion (offset from reference) in blood glucose per unit impulse dose $U_0$, can be used. The steady-state blood-glucose value, $y_\infty$, can be approximated from the pharmacodynamics of insulin, which is available in the literature. Augmenting the scaled $q_k$-system of (20) to the original $y_k$-system of (1), we obtain the single-input multiple-output model given by $$A(z^{-1})y_k = z^{-d}B(z^{-1})u_k + C(z^{-1})w_k, \quad (21)$$

where $y_k = [y_k, q_k]^T$, $w_k$ is a vector of two white-noise sequences, and $$A(z^{-1}) = I_{2 \times 2} + A_1 z^{-1} + A_2 z^{-2} + \ldots + A_n z^{-n},$$

$$B(z^{-1}) = B_0 + B_1 z^{-1} + B_2 z^{-2} + \ldots + B_m z^{-m},$$

$$C(z^{-1}) = I_{2 \times 2} + C_1 z^{-1} + C_2 z^{-2} + \ldots + C_p z^{-p},$$

with $$A_1 = \begin{bmatrix} a_1 & 0 \\ 0 & a_{1_q} \end{bmatrix}, A_2 = \begin{bmatrix} a_i & 0 \\ 0 & a_{2_q} \end{bmatrix} A_i = \begin{bmatrix} a_i & 0 \\ 0 & 0 \end{bmatrix} \forall i > 2,$$

$$B_0 = \begin{bmatrix} b_0 \\ s_f b_{1_q} \end{bmatrix}, B_1 = \begin{bmatrix} b_0 \\ s_f b_{2_q} \end{bmatrix}, B_i = \begin{bmatrix} b_i \\ 0 \end{bmatrix}, \forall i > 1,$$

$$C_i = \begin{bmatrix} c_i & 0 \\ 0 & 0 \end{bmatrix} \forall i > 0,$$

where, for simplicity, the same system delay d of (1) can be assumed between $q_k$ and $u_k$. Coupling between the two systems, via the same input signal, is relevant when solving for the optimal control signal [5], whereby matrix G is merely extended to give an analogous matrix, $G_e$, for the new system, the latter constructed as:

$$G_e = \begin{bmatrix} g_0 & 0 & 0 & \cdots & \cdot \\ g_{0_q} & 0 & 0 & \cdots & \cdot \\ g_1 & g_0 & 0 & \cdots & \cdot \\ g_{1_q} & g_{0_q} & 0 & \cdots & \cdot \\ \cdot & \cdot & \cdot & \cdots & \cdot \\ \cdot & \cdot & \cdot & \cdots & \cdot \\ \cdot & \cdot & \cdot & \cdots & 0 \\ g_{N-1} & g_{N-2} & \cdots & & g_0 \\ g_{(N-1)q} & g_{(N-2)q} & \cdots & & g_{0_q} \end{bmatrix}_{2N \times N},$$

where the $g_{i_q}$-entries pertain to the $q_k$-system and are the analogues of the $g_i$-entries in the $y_k$-system. Vector f is also adjusted accordingly to yield an extended version, $f_e$, which is twice in length. The GPC signal is again given by (17), except that $G_e$ (or its first $N_u$+1 columns for non-square horizons) and $f_e$ are used in lieu of G and f respectively, in addition to using a trivially extended version, $r_e$, for r. The GMV control is recovered by setting $N_y = N_u = N-1 = 0$.

The following describes the use of constraints on the control signals u(t):

Constraints on input-output signals may be enforced to limit them to allowable, possibly subjective, fields of action. The output constraints are not usually explicitly contemplated, but rather implicitly enforced via optimizing the cost function [5]. In general, the input constraints can be described by $$u_{min} \leq u_t \leq u_{max}$$

$$\Delta u_{min} \leq \Delta u_t \leq \Delta u_{max}.$$

Input constraints, such as minimum (basal) and maximum (bolus) doses, or their respective rate of change, may be explicitly enforced, possibly by saturation or clipping. The input constraints may be left for the user to initialize, but may at the same time be stipulated to be less than (and occasionally clipped or overridden by) a maximum allowable value, possibly based on the subject's weight.

Figure 3:
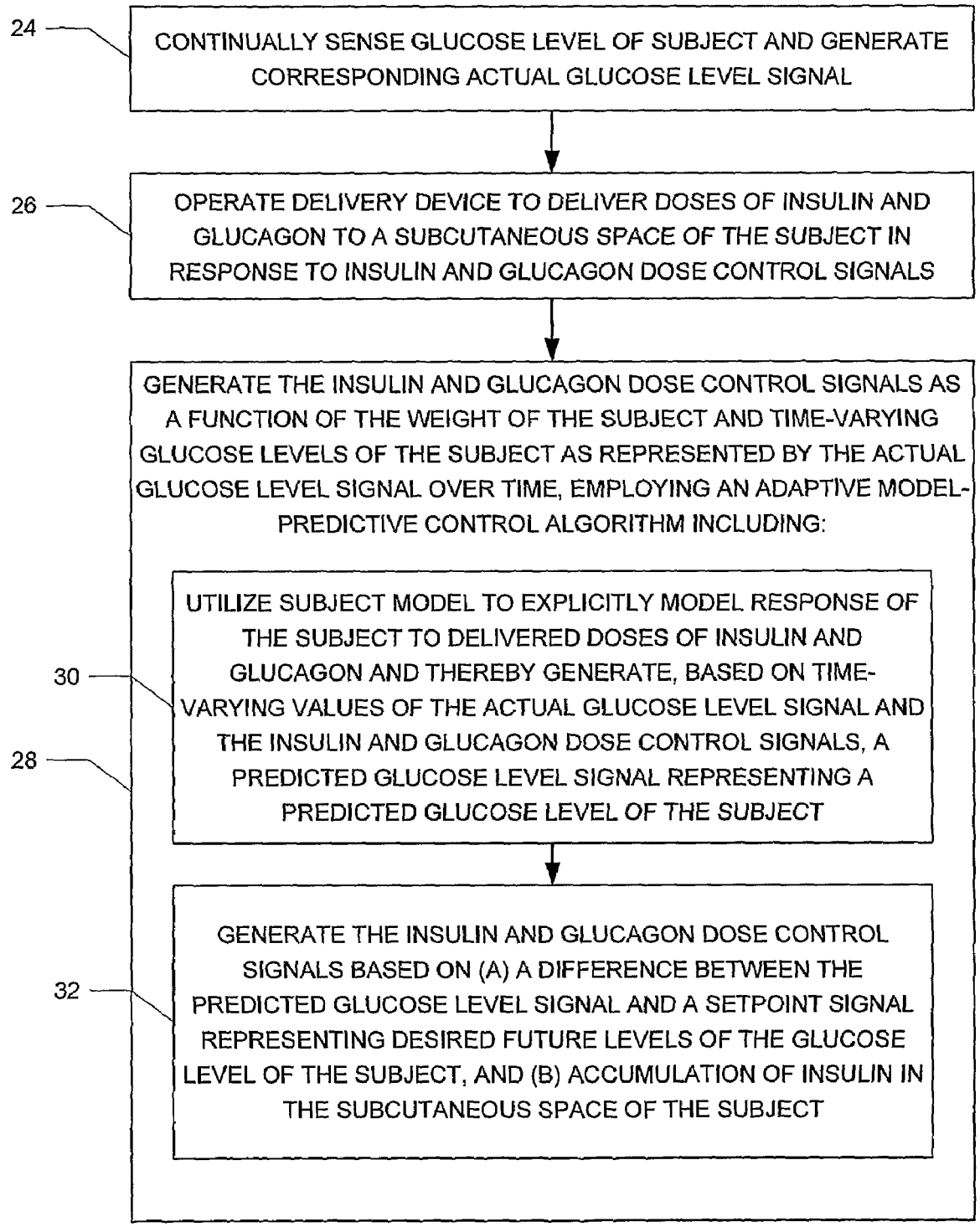
FIG. 3 is a flow diagram depicting the operation of the system of FIG. 1, including details of the operation of the controller of FIG. 2.

FIG. 3 illustrates the overall process by which the system 10 of FIG. 1 operates. In step 24, the glucose level of the subject 12 is continually sensed by the glucose sensor 16, which generates a corresponding actual glucose level signal y(t). In step 26, the delivery device 14 operates in response to the insulin/glucagon dose control signal u(t) to deliver corresponding doses of insulin and glucagon to a subcutaneous space of the subject 12.

In step 28, the controller 18 generates the insulin/glucagon dose control signal u(t) as a function of the weight of the subject 12, the setpoint r(t+k), and time-varying glucose levels of the subject 12 as represented by the actual glucose level signal y(t) over time. Specifically, the controller 18 employs a control algorithm including steps 30 and 32 as shown.

In step 30, a subject model 16 is utilized to explicitly model response of the subject 12 to delivered doses of insulin and glucagon and thereby generate, based on time-varying values of the actual glucose level signal y(t) and the insulin/glucagon dose control signal u(t), a predicted glucose level signal ŷ(t+k|t) representing a predicted glucose level of the subject.

In step 32, the insulin and glucagon dose control signals u(t) are generated based on (a) a difference between the predicted glucose level signal ŷ(t+k|t) and the setpoint signal r(t+k) representing desired future levels of the glucose level of the subject 12, and (b) local accumulation of insulin in the subcutaneous space of the subject 12. This latter value is tracked according to the pharmacokinetics of insulin as described above.

Figure 4:
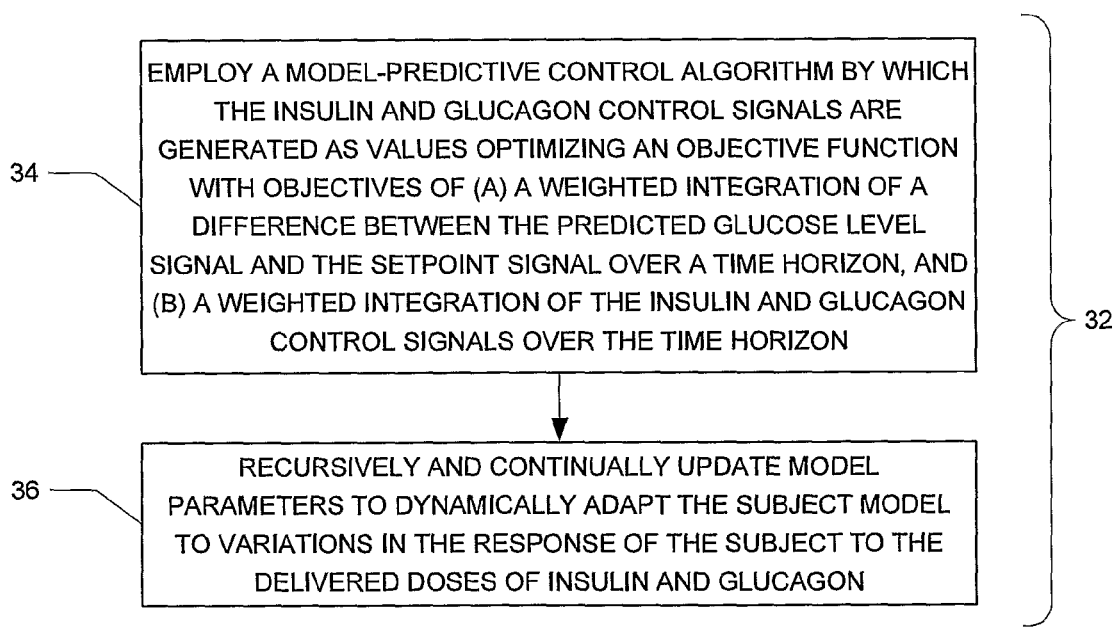
FIG. 4 is a flow diagram depicting a particular implementation of a control step of FIG. 3.

FIG. 4 illustrates a particular implementation of the general step 32 of FIG. 3. In particular, the illustrated embodiment utilizes an MPC control strategy as described above. In step 34, the insulin/glucagon control signal u(t) is generated as optimizing an objective function with objectives of (a) a weighted integration of a difference between the actual glucose level signal y(t) and a predetermined setpoint value over a time horizon, and (b) a weighted integration of the insulin/glucagon control signal u(t) over the time horizon.

In step 36, the model parameters of the subject model 22 are recursively and continually updated to dynamically adapt the subject model 22 to variations in the response of the subject 12 to the delivered doses of insulin and glucagon.

It will be appreciated that the present invention may be embodied as an overall system such as shown in FIG. 1, as an overall method, as a controller such as shown in FIG. 2, and as a method performed by a controller such as shown in FIG. 4. With respect to the method performed by a controller, the method may be performed by computer program instructions executed by generic controller hardware including memory, a processing or execution unit, and input/output circuitry. The instructions may be provided to the controller from a computer-readable medium such as semiconductor memory, magnetic memory (e.g. magnetic disk), optical memory (e.g. optical disk such as CD, DVD), etc.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A system for automatic control of blood glucose level of a subject, comprising:
   a glucose sensor operative to continually sense a glucose level of the subject and generate a corresponding glucose level signal;
   a delivery device operative to deliver doses of insulin to the subject in response to an insulin dose control signal; and
   a controller operative to generate the insulin dose control signal as a function of the weight of the subject and time-varying glucose levels of the subject as represented by the glucose level signal over time, the controller employing a control algorithm including:
      generating the insulin dose control signal based on (a) the glucose level signal, and (b) accumulation of insulin in the subject due to finite rate of utilization,
   wherein the controller employs a model-predictive control algorithm by which the insulin dose control signal is generated as a value optimizing an objective function with objectives of (a) a weighted integration of a difference between a predicted glucose level signal and a setpoint signal over a time horizon, and (b) a weighted integration of the insulin dose control signal over the time horizon.

2. A system according to claim 1, wherein the model-predictive control algorithm is an adaptive model-predictive control algorithm which includes recursively and continually updating model parameters to dynamically adapt the subject model to variations in the response of the subject to the delivered doses of insulin.

3. A system according to claim 1, wherein the objective function is augmented to also have an objective of (c) minimizing the accumulation of insulin in the subject due to finite rate of utilization.

4. A system according to claim 1, wherein:
   (1) the control algorithm includes a subject model to explicitly model response of the subject to delivered doses of insulin and thereby generate, based on time-varying values of the glucose level signal and the insulin dose control signal, the predicted glucose level signal representing a predicted glucose level of the subject; and
   (2) the insulin dose control signal is generated based on a difference between the predicted glucose level signal and the setpoint signal representing a desired glucose level of the subject.

5. A system according to claim 4 wherein the subject model is an empirical subject model.

6. A system according to claim 5, wherein the empirical subject model is of a type initially constructed based on a system identification process performed on input-output data obtained from open-loop glycemic control of the subject.

7. A system according to claim 1 wherein the controller is further operative to generate the insulin dose control signal to provide a basal rate of delivery of insulin when the control algorithm reveals no need for a dose of insulin that exceeds a basal rate of delivery.

8. A system according to claim 7 wherein the basal rate is determined by a user-provided basal-rate value.

9. A system according to claim 8 wherein the controller employs a default basal-rate value based on the weight of the subject when the user-provided basal-rate value is either absent or greater than a predetermined maximum allowable value.

10. A system according to claim 9 wherein the controller adapts the basal rate online based on the glucose level signal over time.

11. A system according to claim 10 wherein the controller is operative to automatically impose respective constraints on the insulin dose control signal corresponding to a maximum allowable dose of insulin.

12. A system according to claim 1 wherein the glucose sensor is integrated with the delivery device.

13. A system according to claim 12 wherein the delivery device comprises a mechanically driven infusion mechanism and a cartridge for insulin.

14. A system according to claim 1, wherein:
the delivery device is further operative to deliver doses of a counter-regulatory agent to the subject in response to a counter-regulatory-agent dose control signal; and
the controller is further operative to generate the counter-regulatory-agent dose control signal as a function of the weight of the subject and the time-varying glucose levels of the subject as represented by the glucose level signal over time.

15. A system according to claim 14 wherein the counter-regulatory agent comprises glucagon.

16. A system according to claim 14 wherein generating the counter-regulatory-agent dose control signal accounts for accumulation in the subject from past doses of the counter-regulatory agent.

17. A system according to claim 1, wherein delivery by the delivery device is to a subcutaneous space in the subject.

18. A system according to claim 1 wherein the generating of the insulin dose control signal based on the accumulation of insulin in the subject provides a controlling effect on aggressiveness of the control algorithm.

19. A system according to claim 1 wherein generating the insulin dose control signal is performed based on a combination of one or more first mathematical expressions of a relationship between the insulin dose control signal and the glucose level signal and one or more second mathematical expressions of an estimation of the accumulation of insulin in the subject based on the insulin dose control signal.

20. A system according to claim 19 wherein generating the insulin dose control signal based on the glucose level signal includes scaled summations of past and ongoing components of the insulin dose control signal and the glucose level signal, and wherein the estimation of the accumulation of insulin in the subject is obtained based on a scaled summation of accumulation contributions based on the insulin dose control signal, including past, ongoing, and/or future components of the insulin dose control signal.

21. A system according to claim 19 wherein the estimation of the accumulation of insulin in the subject is obtained by feedback of the insulin dose control signal.

22. A system according to claim 19 wherein the first and second mathematical expressions are used to obtain a control objective.

23. A method for automatic control of the blood glucose level of a subject, comprising:
continually sensing a glucose level of the subject and generating a corresponding glucose level signal;
operating a delivery device to deliver doses of insulin to the subject in response to an insulin dose control signal; and
generating the insulin dose control signal as a function of the weight of the subject and time-varying glucose levels of the subject as represented by the glucose level signal over time, by a control algorithm including:
generating the insulin dose control signal based on (a) the glucose level signal, and (b) accumulation of insulin in the subject due to finite rate of utilization,
wherein the control algorithm includes a model-predictive control algorithm by which the insulin dose control signal is generated as a value optimizing an objective function with objectives of (a) a weighted integration of a difference between a predicted glucose level signal and a setpoint signal over a time horizon, and (b) a weighted integration of the insulin dose control signal over the time horizon.

24. A method according to claim 23, wherein the model-predictive control algorithm is an adaptive model-predictive control algorithm which includes recursively and continually updating model parameters to dynamically adapt the subject model to variations in the response of the subject to the delivered doses of insulin.

25. A method according to claim 23, wherein the objective function is augmented to also have an objective of (c) minimizing the accumulation of insulin in the subject due to finite rate of utilization.

26. A method according to claim 23, wherein:
(1) the control algorithm includes utilizing a subject model to explicitly model response of the subject to delivered doses of insulin and thereby generate, based on time-varying values of the glucose level signal and the insulin dose control signal, the predicted glucose level signal representing a predicted glucose level of the subject; and
(2) the insulin dose control signal is generated based on a difference between the predicted glucose level signal and the setpoint signal representing a desired glucose level of the subject.

27. A method according to claim 26 wherein the subject model is an empirical subject model.

28. A method according to claim 27, wherein the empirical subject model is initially constructed based on a system identification process performed on input-output data obtained from open-loop glycemic control of the subject.

29. A method according to claim 23 further comprising generating the insulin dose control signal to provide a basal rate of delivery of insulin when the control algorithm reveals no need for a dose of insulin that exceeds a basal rate of delivery.

30. A method according to claim 29 wherein the basal rate is determined by a user-provided basal-rate value.

31. A method according to claim 30 wherein a default basal-rate value based on the weight of the subject is employed when the user-provided basal-rate value is either absent or greater than a predetermined maximum allowable value.

32. A method according to claim 31 wherein the basal rate is adapted online based on the glucose level signal over time.

33. A method according to claim 32 further comprising automatically imposing constraints on the insulin dose control signal corresponding to a maximum allowable dose of insulin.

34. A method according to claim 23, further comprising:
operating the delivery device to deliver doses of a counter-regulatory agent to the subject in response to a counter-regulatory-agent dose control signal; and
generating the counter-regulatory-agent dose control signal as a function of the weight of the subject and the time-varying glucose levels of the subject as represented by the glucose level signal over time.

35. A method according to claim 34 wherein the counter-regulatory agent comprises glucagon.

36. A method according to claim 34 wherein generating the counter-regulatory-agent dose control signal accounts for accumulation in the subject from past doses of the counter-regulatory agent.

37. A method according to claim 23, wherein delivery by the delivery device is to a subcutaneous space in the subject.

38. A method according to claim 23 wherein the generating of the insulin dose control signal based on (b) accumulation of insulin in the subject provides a controlling effect on aggressiveness of the control algorithm.

39. A method according to claim 23 wherein generating the insulin dose control signal is performed based on a combination of one or more first mathematical expressions of a relationship between the insulin dose control signal and the glucose level signal and one or more second mathematical expressions of an estimation of the accumulation of insulin in the subject based on the insulin dose control signal.

40. A method according to claim 39 wherein the relationship between the insulin dose control signal and the glucose level signal includes scaled summations of past and ongoing components of the insulin dose control signal and the glucose level signal, and wherein the estimation of the accumulation of insulin in the subject is obtained based on a scaled summation of accumulation contributions based on the insulin dose control signal, including past, ongoing, and/or future components of the insulin dose control signal.

41. A method according to claim 39 wherein the estimation of the accumulation of insulin in the subject is obtained by feedback of the insulin dose control signal.

42. A method according to claim 39 wherein the first and second mathematical expressions are used to obtain a control objective.

43. A controller for use in a system for automatic control of blood glucose level of a subject, the controller being operative to generate an insulin dose control signal as a function of the weight of the subject and time-varying glucose levels of the subject as represented by an glucose level signal over time, the glucose level signal being generated by a glucose sensor operative to continually sense a glucose level of the subject, the insulin dose control signal controlling the delivery of doses of insulin to the subject by a delivery device, the controller employing a control algorithm including:
  generating the insulin dose control signal based on (a) the glucose level signal, and (b) accumulation of insulin in the subject due to finite rate of utilization,
  wherein the control algorithm includes a model-predictive control algorithm by which the insulin dose control signal is generated as a value optimizing an objective function with objectives of (a) a weighted integration of a difference between a predicted glucose level signal and a setpoint signal over a time horizon, and (b) a weighted integration of the insulin dose control signal over the time horizon.

44. A controller according to claim 43, wherein the model-predictive control algorithm is an adaptive model-predictive control algorithm which includes recursively and continually updating model parameters to dynamically adapt the subject model to variations in the response of the subject to the delivered doses of insulin.

45. A controller according to claim 43, wherein the objective function is augmented to also have an objective of (c) minimizing the accumulation of insulin in the subject due to finite rate of utilization.

* * * * *